(12) United States Patent
Suzuki et al.

(10) Patent No.: US 11,612,891 B2
(45) Date of Patent: Mar. 28, 2023

(54) FILTER FILM AND USE THEREOF

(71) Applicant: TOKYO OHKA KOGYO CO., LTD., Kawasaki (JP)

(72) Inventors: Yasuo Suzuki, Kawasaki (JP); Atsushi Murota, Kawasaki (JP); Takashi Ohsaka, Kawasaki (JP); Toshiyuki Ogata, Kawasaki (JP)

(73) Assignee: TOKYO OHKA KOGYO CO., LTD., Kawasaki (JP)

( * ) Notice: Subject to any disclaimer, the term of this patent is extended or adjusted under 35 U.S.C. 154(b) by 1010 days.

(21) Appl. No.: 16/387,298

(22) Filed: Apr. 17, 2019

(65) Prior Publication Data

US 2019/0344275 A1 Nov. 14, 2019

(30) Foreign Application Priority Data

May 11, 2018 (JP) .............................. JP2018-092040

(51) Int. Cl.
*B01L 3/00* (2006.01)
*G01N 33/543* (2006.01)

(52) U.S. Cl.
CPC ........... *B01L 3/502761* (2013.01); *G01N 33/54386* (2013.01); *B01L 2200/0652* (2013.01); *B01L 2200/12* (2013.01); *B01L 2300/0681* (2013.01); *B01L 2300/0864* (2013.01); *B01L 2300/0887* (2013.01)

(58) Field of Classification Search
USPC ...................................................... 435/7.21
See application file for complete search history.

(56) References Cited

U.S. PATENT DOCUMENTS

| | | | | |
|---|---|---|---|---|
| 8,877,141 | B2 * | 11/2014 | Yu .................. | B01L 3/5085 422/407 |
| 10,466,160 | B2 * | 11/2019 | Handique ............ | G06V 10/147 |
| 2007/0190522 | A1 * | 8/2007 | Somack ................. | B01D 61/00 435/2 |
| 2011/0294678 | A1 | 12/2011 | Jin et al. | |
| 2012/0183977 | A1 * | 7/2012 | Bunce ................... | B01L 3/5085 435/7.92 |
| 2014/0339165 | A1 | 11/2014 | Han et al. | |
| 2015/0160135 | A1 | 6/2015 | Tibbe et al. | |
| 2016/0136552 | A1 * | 5/2016 | Nakanishi ............... | A61M 1/34 210/695 |
| 2016/0279898 | A1 | 9/2016 | Senzaki et al. | |
| 2016/0348050 | A1 | 12/2016 | Sivan et al. | |
| 2017/0198246 | A1 * | 7/2017 | Niazi .................... | C12M 41/00 |
| 2018/0282677 | A1 | 10/2018 | Ohsaka et al. | |
| 2019/0225927 | A1 | 7/2019 | Ohsaka et al. | |

FOREIGN PATENT DOCUMENTS

| | | |
|---|---|---|
| EP | 1295846 A1 | 3/2003 |
| EP | 2977099 A1 | 1/2016 |
| JP | 4148367 B | 9/2008 |
| JP | 5278913 B | 9/2013 |
| JP | 2014-223621 A | 12/2014 |
| JP | 2015-521103 A | 7/2015 |
| JP | 2016-182553 A | 10/2016 |
| JP | 2018-034087 A | 3/2018 |
| WO | WO 2013/173631 A2 | 11/2013 |
| WO | WO 2017/057234 A1 | 4/2017 |
| WO | WO 2018/061973 A1 | 4/2018 |

OTHER PUBLICATIONS

Office Action In Japanese Patent Application No. 2018-092040 dated Nov. 30, 2021.
Search Report issued in European Patent application No. 19170160. 6, dated Jun. 21, 2019.

* cited by examiner

*Primary Examiner* — Ann Montgomery
(74) *Attorney, Agent, or Firm* — Knobbe, Martens, Olson & Bear LLP (57) ABSTRACT

A filter film includes a through-hole and a recessed portion having a size capable of capturing one particle, in which the recessed portion is open to one face of the filter film, the through-hole in the one face has a shape or a size such that the one particle is not capable of passing through the through-hole, and the through-hole and the recessed portion are disposed close to each other.

13 Claims, 7 Drawing Sheets

FILTER FILM AND USE THEREOF

RELATED APPLICATION

This application claims priority to Japanese Patent Application No. 2018-092040, filed May 11, 2018, the entire contents of which are incorporated herein by reference.

BACKGROUND OF THE INVENTION

Field of the Invention

An aspect of the present invention relates to a filter film and use thereof. More specifically, the present invention relates to a filter film, a method of manufacturing a filter film, a structure body, a method of capturing a particle, and a method of sorting cells.

Description of Related Art

There is a demand for capture and comprehensive analysis of particles such as cells. For example, particularly in the field of drug discovery, it has been attempted to sort and recover cells at the single cell level and use the recovered cells. As a method of sorting cells, for example, a method, in which a secretion secreted from cells is detected and cells which secrete the target secretion are specified, is carried out. In such a single cell analysis, a technique for comprehensively capturing cells and collectively analyzing the cells is useful.

As a method of comprehensively capturing cells, for example, Japanese Patent No. 5278913 discloses a device capable of capturing cells at a single cell level on a micromesh having a plurality of fine through-holes for capturing cells.

Also, there is known a method in which a large number of single cells are simultaneously analyzed using a microchip having a well sized to contain only one cell. For example, Japanese Patent No. 4148367 discloses a microwell array having wells each sized to contain only one cell and a screening method in which cells are cultured in the microwell array and a substance produced from the cells stored in the wells is detected.

SUMMARY OF THE INVENTION

However, in the device disclosed in Japanese Patent No. 5278913, the cells captured on the micromesh are fixed to openings of the fine through-holes by only an attraction force. Therefore, the captured cells may move out of capture positions during operation, in some cases. Also, in the method described in Japanese Patent No. 4148367, it may take time to store the cells in the well, in some cases.

Thus, an object of the present invention is to provide a technology to efficiently capture particles.

The present invention includes the following aspects.

According to a first aspect of the present invention, there is provided a filter film including a through-hole and a recessed portion having a size capable of capturing one particle, in which the recessed portion is open to one face of the filter film, the through-hole in the one face has a shape or a size such that the one particle is not capable of passing through the through-hole, and the through-hole and the recessed portion are disposed close to each other.

According to a second aspect of the present invention, there is provided a method of manufacturing the filter film, the method including: laminating a dissolvable base film on a support; laminating a first curable resin film on the base film; patterning the first curable resin film to obtain a first film in which a first through-hole and a bottom of the recessed portion are patterned; laminating a second curable resin film on the first film; patterning the second curable resin film to obtain a second film in which a second through-hole continuous with the first through-hole and a side portion of the recessed portion are patterned; and dissolving the base film to separate a laminate of the first film and the second film, which is to be the filter film, from the support.

According to a third aspect of the present invention, there is provided a structure body including: the filter film; and a substrate disposed apart from the filter film so as to face the other face of the filter film.

According to a fourth aspect of the present invention, there is provided a method of capturing particles, including: bringing a dispersion liquid of the particle into contact with a face of the filter film on the side to which the recessed portion is open.

According to a fifth aspect of the present invention, there is provided a method of sorting cells, by which a target cell secreting a secretion is sorted from a plurality of cells, the method including: bringing a dispersion liquid of the cells into contact with a face, of the filter film of the structure body, on a side to which the recessed portion is open, to capture one unit of the cells per the recessed portion; causing the cells captured in the recessed portion to secrete the secretion and causing the secretion to be accumulated on an area, of a surface of the substrate, close to the recessed portion; detecting a change caused by accumulation of the secretion; and sorting the target cell using the change as an index.

According to the present invention, it is possible to provide a technology to efficiently capture particles.

DETAILED DESCRIPTION OF THE INVENTION

Hereinafter, embodiments of the present invention will be described in detail with reference to the drawings in some cases. In the drawings, the same or corresponding parts are denoted by the same or corresponding references, and duplicated description will not be repeated. A dimensional ratio in each drawing is exaggerated for explanation and does not necessarily coincide with an actual dimensional ratio.

Filter Film

A filter film of the present embodiment includes a through-hole and a recessed portion having a size capable of capturing one particle, in which the recessed portion is open to one face of the filter film, the through-hole in the one face has a shape or a size such that the one particle is not capable of passing through the through-hole, and the through-hole and the recessed portion are disposed close to each other. The material of the filter film will be described later.

As will be described later in Examples, according to the filter film of the present embodiment, it is possible to efficiently capture particles. In the present specification, the expression "efficiently capture particles" means that, for example, in a case where a dispersion liquid of particles is brought into contact with a filter film, the particles in contact with the filter film are accommodated in recessed portions at a high rate within a unit time.

Figure 1A:
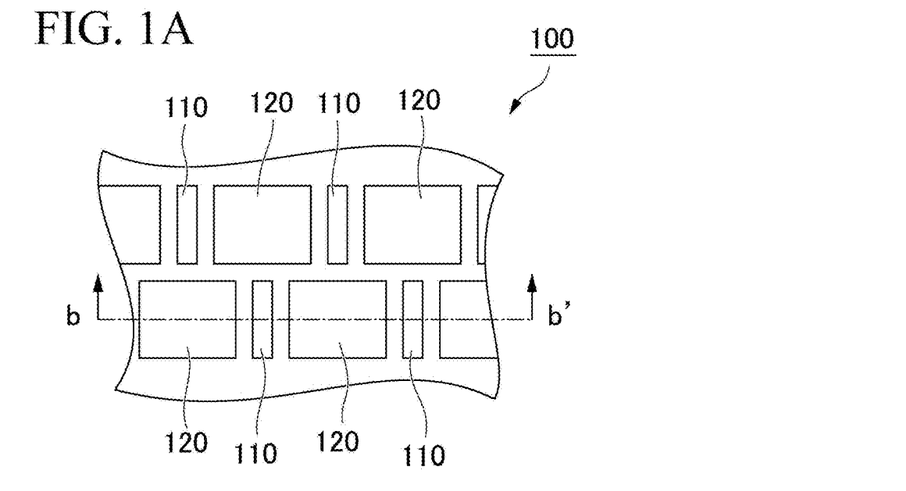
FIG. 1A is a top view of a filter film according to an embodiment.
Figure 1B:
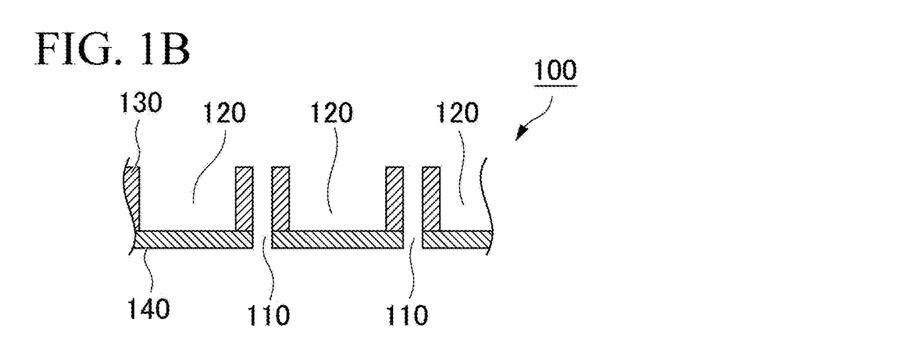
FIG. 1B is a sectional view taken along line b-b' of FIG. 1A.
Figure 1C:
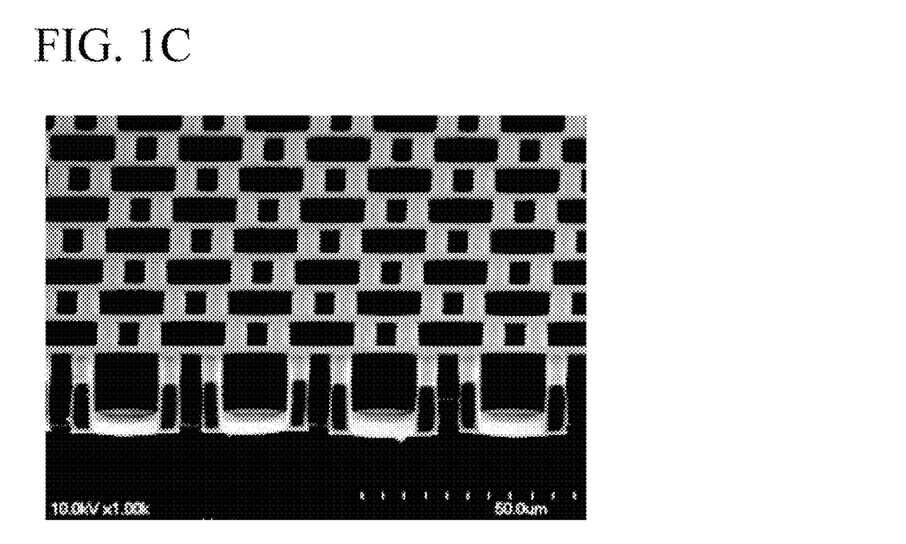
FIG. 1C is an electron micrograph of a filter film manufactured in an Example.

FIG. 1A is a top view of a filter film 100, which is an example of the filter film of the present embodiment. FIG. 1B is a sectional view taken along the line b-b' of the filter film 100 shown in FIG. 1A. FIG. 1C is an electron micrograph of the filter film 100, which is shown in FIGS. 1A and 1B and manufactured in practice in Example to be described later. In FIG. 1C, a sectional face and a top face of the filter film 100 are photographed.

The filter film 100 has a through-hole 110 and a recessed portion 120. The recessed portion 120 has a size capable of capturing one particle. The recessed portion 120 is open to one face 130 of the filter film 100. The through-hole 110 in the one face 130 has a size such that the one particle is not capable of passing through the through-hole. The through-hole 110 and the recessed portion 120 are disposed close to each other.

In the filter film 100, a shape or size of the through-hole 110 is to an extent that the one particle cannot pass through, which is not particularly limited as long as one particle cannot pass through the through-hole 110. For example, the shape of the through-hole 110 on the face 130 may be a shape due to which the one particle cannot pass through. Examples of the shape due to which the one particle cannot pass through include a comb shape. Alternatively, a size of the through-hole 110 in the face 130 may be a size due to which the one particle cannot pass through. The size of the through-hole may be, for example, a sectional area of a section (a section parallel to the face 130) of the through-hole 110 on the face 130.

In addition, the shape of the through-hole 110 is not particularly limited. For example, the shape of the through-hole 110 may be cylindrical, a polyhedron having a plurality of faces (such as a rectangular parallelepiped, a hexagonal prism, or an octagonal prism), a truncated cone shape, truncated pyramidal trapezoid (such as triangular pyramidal trapezoid, quadrangular pyramidal trapezoid, pentagonal pyramidal trapezoid, hexagonal pyramidal trapezoid, or polygonal pyramidal trapezoid with seven or more angles), an inverted truncated cone shape, inverted truncated pyramidal trapezoid (such as inverted triangular pyramidal trapezoid, inverted quadrangular pyramidal trapezoid, inverted pentagonal pyramidal trapezoid, inverted hexagonal pyramidal trapezoid, or inverted polygonal pyramidal trapezoid with seven or more angles), or a shape combining two or more of these shapes. In addition, in the filter film 100, the through-hole 110 may be only one of the shapes or may be a combination of two or more of the shapes.

The shape of the recessed portion 120 is not particularly limited, and may be the same as the above-described shape of the through-hole 110. In addition, in the filter film 100, the recessed portion 120 may be only one of the shapes or may be a combination of two or more of the shapes.

In addition, the shapes and sizes of the through-holes 110 may be the same as each other or different from each other throughout the filter film 100. However, it is preferable that the shapes and sizes are the same as each other. Similarly, the shapes and sizes of the recessed portions 120 may be the same as each other or different from each other throughout the filter film 100. However, it is preferable that the shapes and sizes are the same as each other.

The expression that the through-hole 110 and the recessed portion 120 are disposed close to each other in the filter film 100 means that a distance between a centroid of the shape of the through-hole 110 on the face 130 and a centroid of the shape of the recessed portion 120 on the face 130 is 0.5 to 10 times the diameter of a circle having the same area as the projected area of the particle (hereinafter, referred to as "projected area-equivalent diameter" in some cases).

In the filter film 100, disposition of the through-hole 110 and the recessed portion 120 is not particularly limited, as long as they are close to each other.

Figure 2A:
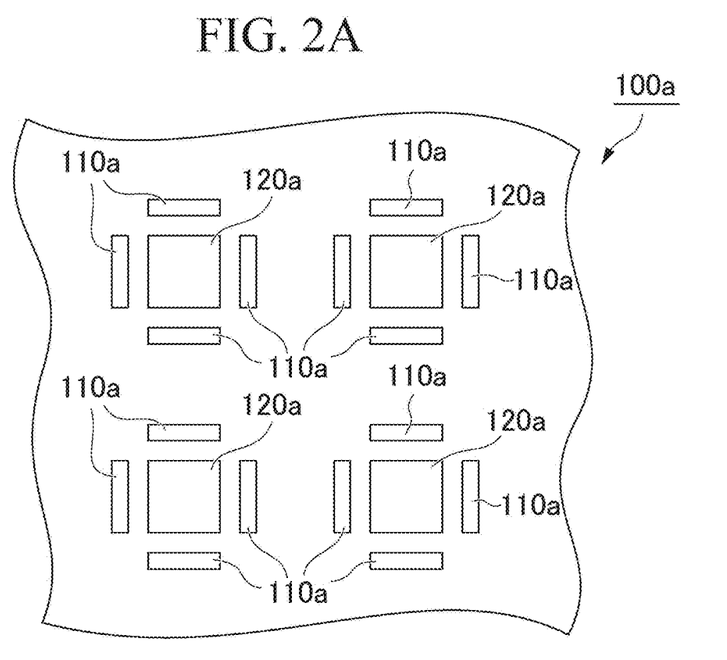
FIG. 2A is a top view of a filter film according to another embodiment.

FIG. 2A is a top view of a filter film 100a, which is an example of the filter film of the present embodiment. The filter film 100a has a through-hole 110a and a recessed portion 120a. The through-hole 110a and the recessed portion 120a may be, for example, disposed as shown in FIG. 2A, and a disposition thereof is not limited thereto.

Figure 2B:
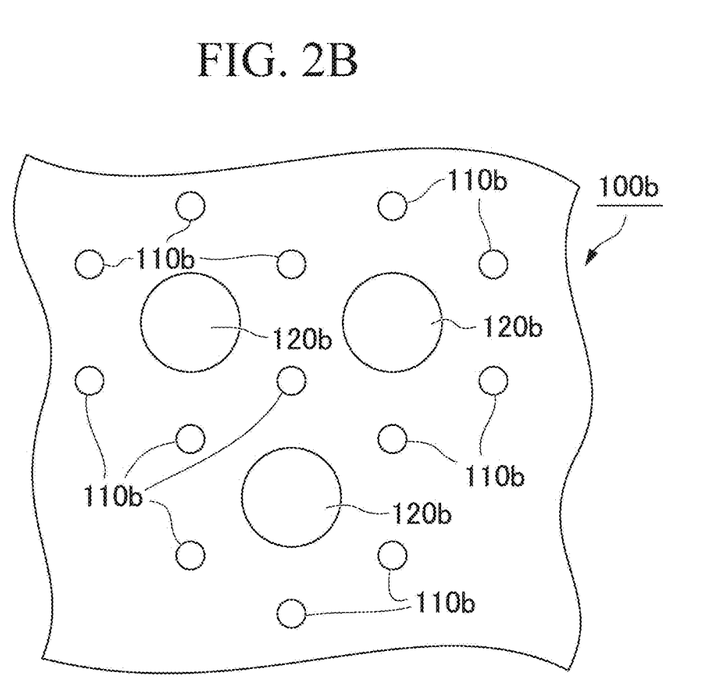
FIG. 2B is a top view of a filter film according to still another embodiment.

FIG. 2B is a top view of a filter film 100b, which is an example of the filter film of the present embodiment. The filter film 100b has a through-hole 110b and a recessed portion 120b. The through-hole 110b and the recessed portion 120b may be, for example, disposed as shown in FIG. 2B, and the disposition thereof is not limited thereto.

The filter film 100 of the present embodiment may have a plurality of the through-holes 110 and a plurality of the recessed portions 120, in which a ratio (through-holes: recessed portions) between the number of the through-holes 110 and the number of the recessed portions 120 may be 1:5 to 100:1.

The ratio between the number of the through-holes 110 and the number of the recessed portions 120 is preferably 1:5 to 10:1, and more preferably 1:4 to 4:1.

Particle

In the present specification, the particle is not particularly limited, and examples thereof include a cell, a cell mass, a resin particle, a metal particle, a glass particle, and a ceramic particle. In the present specification, in a case where particles aggregate to form an agglomerate, the agglomerate is referred to as one particle. The projected area-equivalent diameter of one particle (the diameter of a circle having the same area as the projected area of the particle) is not particularly limited, and may be, for example, 0.01 μm or more and 1 mm or less. Also, it may be, for example, 1 to 500 μm, 1 to 200 μm, 1 to 100 μm, or 1 to 50 μm.

Application of Filter Film

As described above, examples of the particle may include a cell. In addition, the filter film may also be used for capturing a cell. That is, the filter film of the present embodiment may also be a cell capturing filter film. As will be described later in Examples, the filter film of the present embodiment can efficiently capture cells.

Method of Manufacturing Filter Film

A method of manufacturing the filter film of the present embodiment includes: laminating a dissolvable base film on a support (hereinafter referred to as "Step 1"); laminating a first curable resin film on the base film (hereinafter referred to as "Step 2"); patterning the first curable resin film to obtain a first film in which a first through-hole and a bottom of the recessed portion are patterned (hereinafter referred to as "Step 3"); laminating a second curable resin film on the first film (hereinafter referred to as "Step 4"); patterning the second curable resin film to obtain a second film in which a second through-hole continuous with the first through-hole and a side portion of the recessed portion are patterned (hereinafter referred to as "Step 5"); and dissolving the base film to separate a laminate of the first film and the second film, which is to be the filter film, from the support (hereinafter referred to as "Step 6"). According to the manufacturing method of the present embodiment, the above-described filter film can be manufactured. FIGS. 3(a) to (f) are schematic views showing the method of manufacturing the filter film. Hereinafter, the manufacturing method of the present embodiment will be described with reference to FIGS. 3(a) to (f).

Step 1

Figure 3:
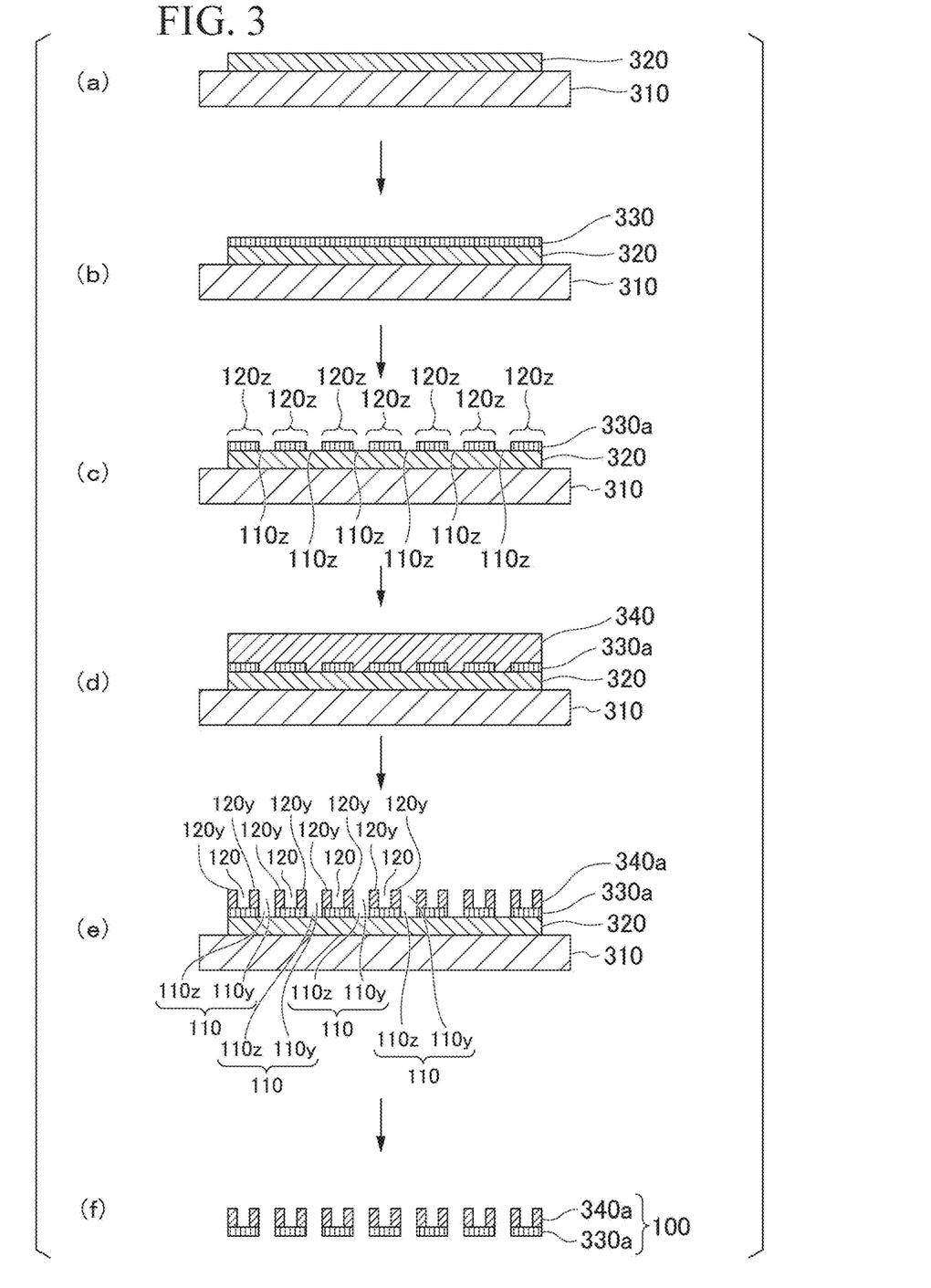
FIGS. 3(a) to (f) are schematic views showing a method of manufacturing a filter film.

As shown in FIG. 3(a), in this step, a base film 320 which is dissolvable is laminated on a support 310. As the support 310, for example, a substrate and the like used for an electronic component are exemplary examples. More specifically, examples thereof include a substrate made of a metal such as a silicon wafer, copper, chromium, iron, or aluminum, or a glass substrate.

As the base film 320, for example, polyvinyl alcohol resin, dextrin, gelatin, glue, casein, shellac, gum arabic, starch, protein, polyacrylic acid amide, sodium polyacrylate, polyvinyl methyl ether, styrene elastomer, a copolymer of methyl vinyl ether and maleic anhydride, a copolymer of vinyl acetate and itaconic acid, polyvinyl pyrrolidone, acetyl cellulose, hydroxyethyl cellulose, and sodium alginate can be used. These materials may be used in a combination of a plurality of materials soluble in the same kind of liquid. From the viewpoint of strength and flexibility of the base film, the material of the base film may contain, for example, polysaccharides such as mannan and xanthan gum and may also contain a rubber component such as guar gum.

Specifically, the base film 320 can be laminated on the support 310 by coating the support 310 with a base film forming composition.

Step 2

As shown in FIG. 3(b), in this step, a first curable resin film 330 is laminated on the support 320. Specifically, the curable resin film 330 can be laminated on the base film 320 by coating the base film 320 with a curable resin composition.

Examples of the curable resin composition include those having a curing property by crosslinking by irradiation with an active energy ray such as ultraviolet ray, and for example, a negative photoresist.

More specific examples of the curable resin composition include an epoxy-functional novolak resin, a cationic photoinitiator such as triarylsulfonium salt, and diluent capable of reacting with an epoxy functional group, and also include a photocurable composition which is completely cured to be a resin which is difficult to separate.

As the curable resin composition, for example, a resin composition including (a) a multifunctional epoxy resin, (b) a cationic polymerization initiator, and (c) a solvent can be suitably used.

(a) Multifunctional Epoxy Resin

The polyfunctional epoxy resin is a resin having two or more epoxy groups in one molecule, and may be any epoxy resin as long as it is an epoxy resin containing a sufficient number of epoxy groups for curing a resin film formed of a curable resin composition in one molecule. Examples of the polyfunctional epoxy resin include a phenol novolak epoxy resin, an orthocresol novolak epoxy resin, a triphenyl novolak epoxy resin, and a bisphenol A novolak epoxy resin.

Functionality, which is the number of epoxy groups contained in one molecule of the polyfunctional epoxy resin, is preferably 2 or more, and more preferably 3 to 12. Since a resin pattern having a high aspect ratio and resolution can be formed, it is preferable that the functionality of the polyfunctional epoxy resin is 3 or more. Since it is easy to control resin synthesis and is possible to prevent internal stress of the resin pattern from becoming excessively large, it is preferable that the functionality of the polyfunctional epoxy resin is 12 or less.

The mass average molecular weight of the polyfunctional epoxy resin is preferably 300 to 5000, and more preferably 500 to 4000. When the mass average molecular weight of the polyfunctional epoxy resin is 300 or more, the curable resin composition can be prevented from thermally flowing before curing by irradiation with an active energy ray, which is preferable. When the mass average molecular weight of the polyfunctional epoxy resin is 5000 or less, an appropriate dissolution rate during patterning development can be obtained, which is preferable.

The amount of the polyfunctional epoxy resin in the curable resin composition is preferably 1% to 99.9% by mass, and more preferably 5% to 70% by mass, in total solid content. Accordingly, it is possible to obtain a curable resin film with high sensitivity and suitable hardness when coating a substrate.

(b) Cationic Polymerization Initiator

The cationic polymerization initiator is a compound in which when irradiated with an active energy ray such as ultraviolet ray, far ultraviolet ray, excimer laser light such as KrF or ArF, X ray, or electron beam, a cation is generated and the cation becomes a polymerization initiator.

Examples of the cationic polymerization initiator include 4-(2-chloro-4-benzoyl phenylthio)phenyldiphenylsulfonium hexafluoroantimonate, 4-(2-chloro-4-benzoyl phenylthio) phenyl bis(4-fluorophenyl)sulfonium hexafluoroantimonate, 4-(2-chloro-4-benzoyl phenylthio)phenyl bis(4-chlorophenyl)sulfonium hexafluoroantimonate, 4-(2-chloro-4-benzoyl phenylthio)phenyl bis(4-methyl phenyl)sulfonium hexafluoroantimonate, 4-(2-chloro-4-benzoyl phenylthio)phenyl bis (4-(β-hydroxyethoxy)phenyOsulfonium hexafluoroantimonate, 4-(2-methyl-4-benzoyl phenylthio)phenyl bis(4-fluorophenyl)sulfonium hexafluoroantimonate, 4-(3-methyl-4-benzoyl phenylthio)phenyl bis(4-fluorophenyl)sulfonium hexafluoroantimonate, 4-(2-fluoro-4-benzoyl phenylthio) phenyl bis(4-fluorophenyl)sulfonium hexafluoroantimonate, 4-(2-methyl-4-benzoyl phenylthio)phenyl bis(4-fluorophenyl)sulfonium hexafluoroantimonate, 4-(2,3,5,6-tetramethyl-4-benzoyl phenylthio)phenyl bis(4-fluorophenyl) sulfonium hexafluoroantimonate, 4-(2,6-dichloro-4-benzoyl phenylthio)phenyl bis(4-fluorophenyl)sulfonium hexafluoroantimonate, 4-(2,6-dimethyl-4-benzoyl phenylthio)phenyl bis(4-fluorophenyl)sulfonium hexafluoroantimonate, 4-(2,3-dimethyl-4-benzoyl phenylthio)phenyl bis(4-fluorophenyl) sulfonium hexafluoroantimonate, 4-(2-methyl-4-benzoyl phenylthio)phenyl bis(4-chlorophenyl)sulfonium hexafluoroantimonate, 4-(3-methyl-4-benzoyl phenylthio)phenyl bis (4-chlorophenyl)sulfonium hexafluoroantimonate, 4-(2- fluoro-4-benzoyl phenylthio)phenyl bis(4-chlorophenyl)sulfonium hexafluoroantimonate, 4-(2-methyl-4-benzoyl phenylthio)phenyl bis(4-chlorophenyl)sulfonium hexafluoroantimonate, 4-(2,3,5,6-tetramethyl-4-benzoyl phenylthio)phenyl bis(4-chlorophenyl)sulfonium hexafluoroantimonate, 4-(2,6-dichloro-4-benzoyl phenylthio)phenyl bis(4-chlorophenyl)sulfonium hexafluoroantimonate, 4-(2,6-dimethyl-4-benzoyl phenylthio)phenyl bis(4-chlorophenyl)sulfonium hexafluoroantimonate, 4-(2,3-dimethyl-4-benzoyl phenylthio)phenyl bis(4-chlorophenyl)sulfonium hexafluoroantimonate, 4-(2-chloro-4-acetyl phenylthio)phenyldiphenylsulfonium hexafluoroantimonate, 4-(2-chloro-4-(4-methylbenzoyl)phenylthio)phenyldiphenylsulfonium hexafluoroantimonate, 4-(2-chloro-4-(4-fluorobenzoyl)phenylthio)phenyldiphenylsulfonium hexafluoroantimonate, 4-(2-chloro-4-(4-methoxybenzoyl)phenylthio)phenyldiphenylsulfonium hexafluoroantimonate, 4-(2-chloro-4-dodecanoyl phenylthio)phenyldiphenylsulfonium hexafluoroantimonate, 4-(2-chloro-4-acetyl phenylthio)phenyl bis(4-fluorophenyl)sulfonium hexafluoroantimonate, 4-(2-chloro-4-(4-methylbenzoyl)phenylthio)phenyl bis(4-fluorophenyl)sulfonium hexafluoroantimonate, 4-(2-chloro-4-(4-fluorobenzoyl)phenylthio)phenyl bis(4-fluorophenyl)sulfonium hexafluoroantimonate, 4-(2-chloro-4-(4-methoxybenzoyl)phenylthio)phenyl bis(4-fluorophenyl)sulfonium hexafluoroantimonate, 4-(2-chloro-4-dodecanoyl phenylthio)phenyl bis(4-fluorophenyl)sulfonium hexafluoroantimonate, 4-(2-chloro-4-acetyl phenylthio)phenyl bis(4-chlorophenyl)sulfonium hexafluoroantimonate, 4-(2-chloro-4-(4-methylbenzoyl)phenylthio)phenyl bis(4-chlorophenyl)sulfonium hexafluoroantimonate, 4-(2-chloro-4-(4-fluorobenzoyl)phenylthio)phenyl bis(4-chlorophenyl)sulfonium hexafluoroantimonate, 4-(2-chloro-4-(4-methoxybenzoyl)phenylthio)phenyl bis(4-chlorophenyl)sulfonium hexafluoroantimonate, 4-(2-chloro-4-dodecanoyl phenylthio)phenyl bis(4-chlorophenyl)sulfonium hexafluoroantimonate, 4-(2-chloro-4-benzoyl phenylthio)phenyldiphenylsulfonium hexafluorophosphate, 4-(2-chloro-4-benzoyl phenylthio)phenyldiphenylsulfonium tetrafluoroborate, 4-(2-chloro-4-benzoyl phenylthio)phenyldiphenylsulfonium perchlorate, 4-(2-chloro-4-benzoyl phenylthio)phenyldiphenylsulfonium trifluoromethanesulfonate, 4-(2-chloro-4-benzoyl phenylthio)phenyl bis(4-fluorophenyl)sulfonium hexafluorophosphate, 4-(2-chloro-4-benzoyl phenylthio)phenyl bis(4-fluorophenyl)sulfonium tetrafluoroborate, 4-(2-chloro-4-benzoyl phenylthio)phenyl bis(4-fluorophenyl)sulfonium perchlorate, 4-(2-chloro-4-benzoyl phenylthio)phenyl bis(4-fluorophenyl)sulfonium trifluoromethanesulfonate, 4-(2-chloro-4-benzoyl phenylthio)phenyl bis(4-fluorophenyl)sulfonium p-toluenesulfonate, 4-(2-chloro-4-benzoyl phenylthio)phenyl bis(4-fluorophenyl)sulfonium camphorsulfonate, 4-(2-chloro-4-benzoyl phenylthio)phenyl bis(4-fluorophenyl)sulfonium nonafluorobutanesulfonate, 4-(2-chloro-4-benzoyl phenylthio)phenyl bis(4-chlorophenyl)sulfonium hexafluorophosphate, 4-(2-chloro-4-benzoyl phenylthio)phenyl bis(4-chlorophenyl)sulfonium tetrafluoroborate, 4-(2-chloro-4-benzoyl phenylthio)phenyl bis(4-chlorophenyl)sulfonium perchlorate, 4-(2-chloro-4-benzoyl phenylthio)phenyl bis(4-chlorophenyl)sulfonium trifluoromethanesulfonate, diphenyl[4-(phenylthio)phenyl]sulfonium trifluorotrispentafluoroethyl phosphate, diphenyl[4-(p-terphenylthio)phenyl]sulfonium hexafluoroantimonate, and diphenyl[4-(p-terphenylthio)phenyl]sulfonium trifluorotrispentafluoroethyl phosphate.

Among these compounds, the 4-(2-chloro-4-benzoyl phenylthio)phenyl bis(4-fluorophenyl)sulfonium hexafluoroantimonate (manufactured by ADEKA CORPORATION, ADEKA OPTOMER SP-172), the diphenyl[4-(phenylthio)phenyl]sulfonium trifluorotrispentafluoroethyl phosphate (manufactured by San-Apro Ltd., CPI-210S), and the diphenyl[4-(p-terphenylthio)phenyl]sulfonium hexafluoroantimonate and the diphenyl[4-(p-terphenylthio)phenyl]sulfonium trifluorotrispentafluoroethyl phosphate (manufactured by San-Apro Ltd., HS-1PG) are preferable.

The amount of the cationic polymerization initiator in the curable resin composition is preferably 0.1% to 10% by mass, and more preferably 0.5% to 5% by mass, in the total solid content. When the amount of the cationic polymerization initiator in the curable resin composition is 0.1% by mass or more, it is possible to make the curing time of the curable resin composition by exposure to active energy ray appropriate. In addition, when the amount of the cationic polymerization initiator in the curable resin composition is 10% by mass or less, developability after exposure to the active energy ray is favorable.

(c) Solvent

As the solvent of the curable resin composition, those commonly used as a solvent for resists can be used without particular limitation, and examples thereof include lactones such as γ-butyrolactone; ketones such as acetone, methyl ethyl ketone (MEK), cyclohexanone, methyl-n-pentyl ketone(2-heptanone), and methyl isopentyl ketone; polyhydric alcohols such as ethylene glycol, diethylene glycol, propylene glycol, and dipropylene glycol; a compound having an ester bond, such as methoxybutyl acetate, ethylene glycol monoacetate, diethylene glycol monoacetate, propylene glycol monoacetate, and dipropylene glycol monoacetate, and derivatives of polyhydric alcohols such as a compound having an ether bond, such as monoalkyl ether or monophenyl ether, such as monomethyl ether, monoethyl ether, monopropyl ether, and monobutyl ether of the polyhydric alcohols or the compound having an ester bond [among these, propylene glycol monomethyl ether acetate (PGMEA) and propylene glycol monomethyl ether (PGME) are preferable]; cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethyl benzyl ether, cresyl methyl ether, diphenyl ether, dibenzyl ether, phenetole, butyl phenyl ether, ethyl benzene, diethyl benzene, pentyl benzene, isopropyl benzene, toluene, xylene, cymene, and mesitylene; and dimethyl sulfoxide (DMSO). Among these, the PGMEA, the PGME, the γ-butyrolactone and the EL are preferable. One kind of the solvents may be used alone and a mixture of two or more kinds thereof may be used.

The amount of the solvent in the curable resin composition is not particularly limited, and may be appropriately set at a concentration at which it is possible to coat the support 310. For example, the content may be set such that the solid content concentration of the curable resin composition is within a range of 1% to 70% by mass.

Step 3

For example, a photomask having a desired pattern shape is placed on the surface of the curable resin film 330 and irradiated with an active energy ray such as an ultraviolet ray. Thereafter, the curable resin film 330 can be patterned by subjecting to a development step and, as needed, a post bake step.

As shown in FIG. 3(c), in this step, the first curable resin film 330 is patterned to obtain a first film 330a in which a first through-hole 110z and a bottom 120z of the recessed portion 120 are patterned.

Step 4

As shown in FIG. 3(d), in this step, a second curable resin film 340 is laminated on the first film 330a. Specifically, the curable resin film 340 can be laminated on the first film 330a by coating the first film 330a with a curable resin composition and volatilizing a solvent component contained in the curable resin composition. In this step, as the curable resin composition, the same compositions as those coating the first curable resin film 330 described above can be used.

Step 5

As shown in FIG. 3(e), in this step, the second curable resin film 340 is patterned to obtain a second film 340a in which a second through-hole 110y continuous with the first through-hole 110z and a side portion 120y of the recessed portion 120 are patterned. The patterning of the curable resin film 340 can be carried out in the same manner as the patterning of the curable resin film 330 described above. The side portion 120y of the recessed portion 120 can be referred to as a wall portion of the recessed portion 120, a side wall portion of the recessed portion 120, or the like.

Here, the first through-hole 110z and the second through-hole 110y continuous therewith configure the through-hole 110 of the filter film 100 shown in FIGS. 1A to 1C. Also, the bottom 120z of the recessed portion 120 and the side portions 120y of the recessed portion 120, which are described above, configure the recessed portion 120 of the filter film 100 shown in FIGS. 1A to 1C.

Step 6

As shown in FIG. 3(e), in this step, the base film 320 is dissolved to separate a laminate of the first film 330a and the second film 340a, which is to be the filter film 100, from the support 310. Dissolution of the base film 320 can be performed by, for example, immersing the structure body obtained in Step 5 in a release agent corresponding to the material of the base film 320.

According to the above steps, it is possible to manufacture the above-described filter film.

Structure Body

A structure body of the present embodiment includes the above-described filter film and a substrate disposed apart from the filter film so as to face the other face of the filter film. As described above, the one face of the filter film is the face to which the recessed portion of the filter film is open.

Figure 4A:
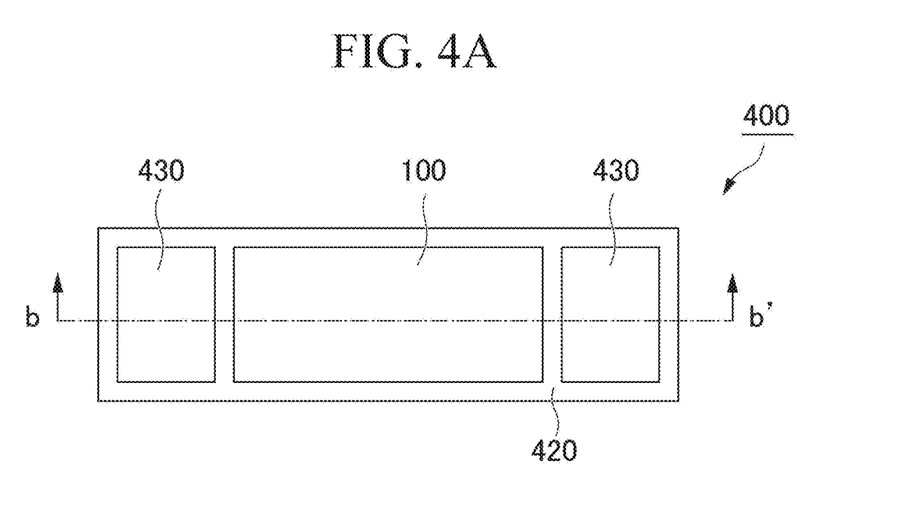
FIG. 4A is a top view of a structure body according to an embodiment.
Figure 4B:
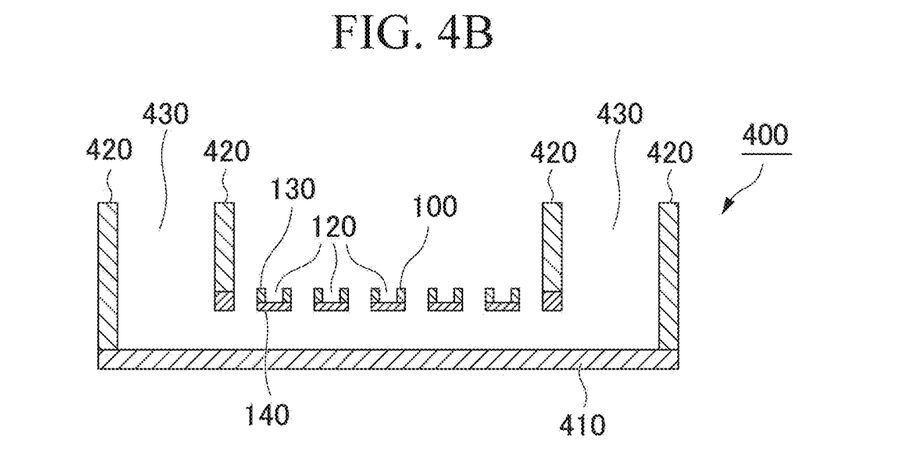
FIG. 4B is a sectional view taken along line b-b' of FIG. 4A.

FIG. 4A is a top view of a structure body 400, which is an example of the structure body of the present embodiment. FIG. 4B is a sectional view taken along the line b-b' of the structure body 400 shown in FIG. 4A. As shown in FIGS. 4A and 4B, the structure body 400 includes the filter film 100 and a substrate 410 disposed apart from the filter film 100 so as to face the other face 140 of the filter film 100.

As shown in FIGS. 4A and 4B, the structure body of the present embodiment may further include a member 420 or the like configuring a frame of the structure body, in addition to the filter film 100 and the substrate 410. In the example of the structure body shown in FIGS. 4A and 4B, the space between the filter film 100 and the substrate 410 functions as a flow channel through which a liquid flows. More specifically, the liquid supplied from the one face side of the filter film 100 passes through the through-hole 110 of the filter film 100, flows into the space between the filter film 100 and the substrate 410, and flows toward an opening 430 of the structure body 400 to be discharged. That is, the opening 430 functions as an outlet for the liquid supplied from the one face side of the filter film 100.

Materials of the substrate 410 and the member 420 are not particularly limited. For example, in a case where a particle is captured and observed with a microscope, it is preferable to use a transparent material. In addition, for example, in a case of capturing particles and then performing fluorescence observation, it is preferable to use a material with less autofluorescence. In addition, in a case of capturing a cell as a particle, it is preferable to use a material having no cytotoxic. Also, it is preferable to use a material with low cell adhesion.

Specific examples of the materials of the substrate 410 and the member 420 include glass, polystyrene, polyethylene terephthalate (PET) resin, polymethyl methacrylate (PMMA) resin, polycarbonate (PC) resin, cycloolefin polymer (COP), and epoxy resin.

In the structure body of the present embodiment, a distance between the filter film 100 and the substrate 410 is not particularly limited, and can be appropriately set according to the purpose. For example, in a case of carrying out a method of sorting cells, to be described later, by using the structure body 400, the distance between the other face 140 of the filter film 100 and the substrate 410 may be, for example, 50 to 1000 μm, and may also be, for example, 100 to 500 μm.

Method of Capturing Particles

A method of capturing particles of the present embodiment includes bringing a dispersion liquid (suspension) of the particles into contact with a face (the one face) of the film described above, on the side to which the recessed portion is open. In the method of the present embodiment, the particle is the same as described above.

Examples of a method of bringing the dispersion liquid of the particle into contact with the one face of the filter film include supplying particles suspended in a dispersion medium (particle dispersion liquid) from an one face 130 side of the filter film 100. The dispersion medium of the particle is not particularly limited, and examples thereof include water, a buffer solution, an isotonic solution, and a medium, which can be appropriately used according to the purpose.

Figure 5A:
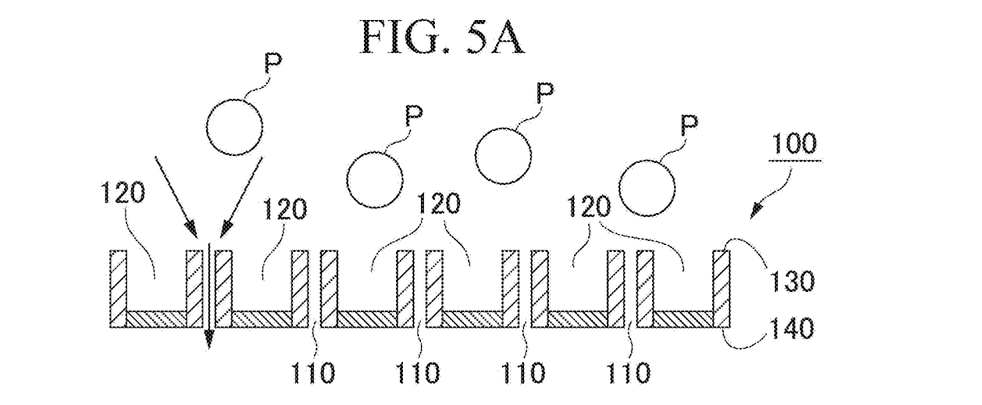
FIGS. 5A to 5C are schematic views showing a method of capturing particles.

FIGS. 5A to 5C are schematic views showing the method of the present embodiment. First, as shown in FIG. 5A, the dispersion liquid of particles P is introduced from the one face 130 side of the filter film 100. As a result, the dispersion medium of the particles P passes through the through-hole 110 and flows out to the other face 140 side of the filter film 100. In FIG. 5A, the arrows indicate the flow of the dispersion medium. The through-hole 110 has a shape or size such that the one particle P is not capable of passing through the through-hole. Therefore, the particles P cannot pass through the through-hole 110, and remain on the one face 130 side of the filter film 100.

Figure 5B:
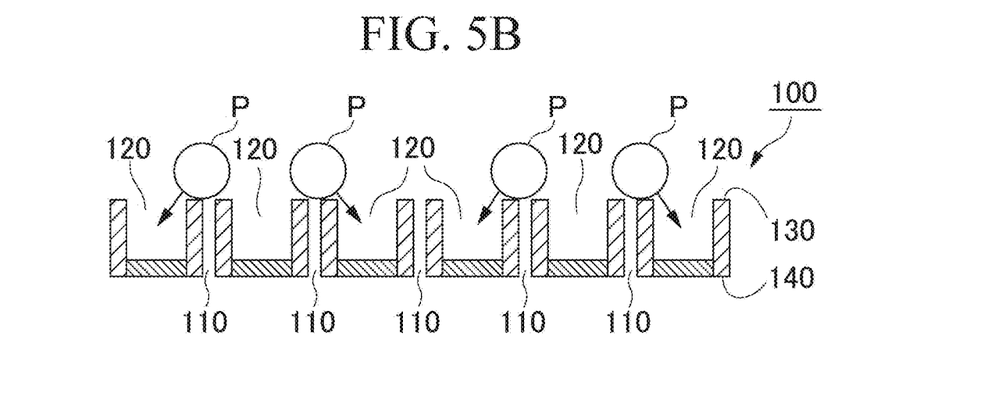
Figure 5C:
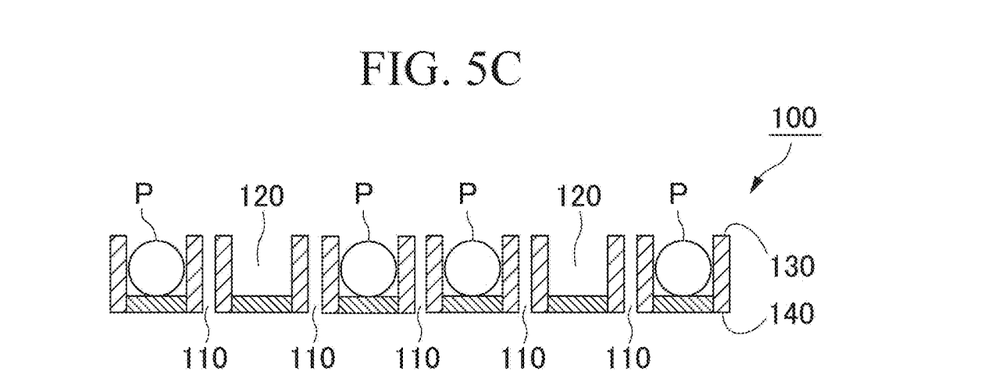

Subsequently, as shown in FIG. 5B, the particles P move along the flow of the dispersion medium to approach the through-hole 110 of the filter film 100. In FIG. 5B, the arrows indicate directions in which the particles move. Subsequently, as shown in FIG. 5C, each particle P close to the through-hole 110 is accommodated in the recessed portion 120 disposed close to the through-hole 110 and captured.

As will be described later in Examples, according to the method of the present embodiment, it is possible to efficiently capture particles. Also, as will be described later in the Examples, examples of the particle may include a cell.

Method of Sorting Cells

A method of sorting cells according to the present embodiment, by which a target cell secreting a secretion is sorted from a plurality of cells, the method includes: bringing a dispersion liquid of the cells into contact with a face (the one face), of the filter film of the structure body, on a side to which the recessed portion is open, to capture one unit of the cells per the recessed portion; causing the cells captured in the recessed portion to secrete the secretion and causing the secretion to be accumulated on an area, of a surface of the substrate, close to the recessed portion; detecting a change caused by accumulation of the secretion; and sorting the target cell using the change as an index.

In the present embodiment, one unit cell means one cell in a case where the cells are dissociated one by one, and means one cell mass in a case where a plurality of cells aggregate to form a cell mass.

The cell forming one unit cell is not particularly limited as long as it is a cell secreting a secretion. Examples thereof include an animal cell (for example, a cell derived from an animal such as human, mouse, goat, sheep, camel, monkey, bird, and shark); a plant cell; an insect cell; fungi such as yeast; and bacteria such as *Escherichia coli*.

In addition, it may also be a cell obtained by introducing a secretory protein, a protein into which a secretory polypeptide or a secretion signal is inserted, or a gene encoding a polypeptide into these cells.

The secretion secreted by the cell may be natural origin or non-natural one using genetic engineering. The secretion is not particularly limited and examples thereof include cytokines such as immunoglobulin G (IgG) and immunoglobulin M (IgM)), interleukin (such as IL-2, IL-7, IL-12, and L-15), chemokine, interferon (such as IFN-γ), a hematopoietic factor (such as colony stimulating factor, granulocyte colony stimulating factor, and erythropoietin), a cell growth factor (epidermal growth factor, fibroblast growth factor, platelet derived growth factor, hepatocyte growth factor, and transforming growth factor), a cytotoxic factor (tumor necrosis factor and lymphotoxin), adipokine (such as leptin secreted from adipose tissue and tumor necrosis factor), and a neurotrophic factor (such as nerve growth factor), metabolic products of microorganisms, such as antibiotics and pigments, peptide hormones or steroid hormones, microbial hormones, secretory proteins, and protein into which a secretion signal is inserted.

Examples of a naturally derived antibody molecule include the immunoglobulin G (IgG) and the immunoglobulin M (IgM). Also, examples of non-naturally derived antibody molecules include antibody fragments such as Fab, scFv, or Diabody, single domain antibodies, and artificial protein molecules having antibody like properties.

Examples of cells that can be used in the present embodiment include cells secreting antibody molecules, cytokine producing cells, and hormone secreting cells.

The cells secreting the antibody molecules are not particularly limited, and examples thereof include antibody-producing cells such as B cells, hybridomas fused with myeloma cells, animal cells into which genes encoding antibodies are introduced, fungi such as yeast, and bacteria such as *Escherichia coli*.

The cytokine producing cells are not particularly limited, and examples thereof include macrophages, B cells, T cells, NK cells, NKT cells, dendritic cells, liver Kupffer cells, stromal cells, fibroblasts, and vascular endothelial cells.

The hormone secreting cells are not particularly limited, and examples thereof include pituitary anterior lobe cells, somatotropin producing cells, lactotropin-producing cells, thyroid stimulating hormone producing cells, gonadotropin-producing cells, corticotropin-producing cells, intermediate pituitary cells, cells secreting melanocyte-stimulating hormone, oxytocin secreting cells, vasopressin secretory cells, serotonin secreting cells, endorphin secreting cells, somatostatin secreting cells, gastrin secreting cells, secretin secreting cells, cholecystokinin secreting cells, insulin secreting cells, glucagon secreting cells, bombesin secreting cells, thyroid cells, thyroid epithelial cells, parafollicular cells, parathyroid cells, parathyroid main cells, aerobic cells, adrenal gland cells, chromaffin cells, steroid hormone (mineralocorticoid or glucocorticoid) producing cells, testosterone secreting cells, estrogen secreting cells, Progesterone secreting cells, cells of the juxtaglomerular apparatus of the kidney, dense plaque cells of the kidney, peripheral polar cells of the kidney, and mesangial cells of the kidney.

In the method of the present embodiment, the structure body may have, for example, the same structure as the structure body 400 shown in FIGS. 4A and 4B. In the method of the present embodiment, one unit of the above cells is captured per the recessed portion of the filter film of the structure body. Subsequently, the cells captured in the recessed portion are caused to secrete a secretion. As a result, the secretion accumulates in a region close to the recessed portion of the surface of the substrate 410.

In the present embodiment, the expression "secretion accumulates" can be said that the secretion is contacting, staying, bonding, assembling, or accumulating on the surface of the substrate 410. When the secretion contacts with the surface of the substrate 410, a certain change on the surface of the substrate 410 can be detected.

In the present specification, when a certain change occurs on the surface of the substrate 410 due to the contact or the like with the secretion, it can be said that "respond to a secretion". For example, in a case where cells are disposed on the surface of the substrate 410, examples of an aspect of response to a secretion, include an aspect in which due to contact with the secretion, for example, the morphology of cells disposed on the surface of the substrate 410 changes, cell death occurs, a cell proliferation ability changes, the amount of substance (such as ion and pH) in the cells changes, transcription of the gene in the cell is activated, or the like.

In order to quickly evaluate the secretion secreted by one unit cell captured in the recessed portion of the filter film of the structure body, on the surface of the substrate 410, it is preferable that an evaluation position for the secretion in the substrate 410 and a position of the cell secreting the secretion correspond one to one. Accordingly, it becomes easy to sort a target cell.

It is preferable that a substance having an affinity for the secretion secreted from one unit cell captured in the recessed portion of the filter film is disposed on the surface of the substrate 410. Here, "having an affinity" means binding directly or indirectly.

The substance to be disposed on the surface of the substrate 410 is not particularly limited as long as it binds to the secretion secreted from the cell captured in the recessed portion, and examples thereof include biopolymer or various chemical substances such as cells, polynucleotides, antibodies, peptides, and proteins.

For example, in a case where the secretion is an antibody, the substance disposed on the surface of the substrate 410 includes every substance corresponding to an antigen, and includes peptides, proteins, cells expressing the antigen exogenously or endogenously, and the like.

In the case where an expression site of the antigen is intranuclear or cytoplasmic, it is preferable to use a substance in which the antigen is exposed by dissolving or crushing a cell membrane. In addition, cells exogenously or endogenously expressing the antigen on the cell membrane may be used. In this case, the antibody can access the antigen without dissolving or crushing the cell membrane.

That is, it is preferable that, on the surface of the substrate 410, an expressing cell of a biomolecule having an affinity for the secretion is laminated, the biomolecule having an affinity for the secretion is laminated, or a compound having an affinity for the secretion is laminated.

According to the method of the present embodiment, it is possible to sort, for example, antibody producing cells against a membrane protein. Here, the "membrane protein" means a protein attached to a biological membrane. The membrane protein may penetrate the lipid bilayer membrane, may be an integral membrane protein that binds to the lipid bilayer by a fatty acid chain or the like, or may be a peripheral membrane protein that binds to a hydrophilic part of the lipid bilayer or another membrane protein by noncovalent bond. The membrane protein may be a multi-pass transmembrane type or a single-pass transmembrane type.

Examples of the membrane proteins include a G protein-coupled receptors (GPCR), a ligand-gated ion channel, a voltage-gated ion channel, and a transporter.

It is preferable that the substrate 410 has a flow channel structure for removing substances nonspecifically bound to the surface of the substrate 410. For example, as shown in FIG. 4B, the space between the other face 140 of the filter film 100 and the substrate 410 of the structure body 400 functions as a flow channel through which a liquid flows.

The flow channel through which the liquid flows may be configured to pass a liquid of a detection substance for detecting a change occurring on the surface of the substrate 410, for example, a detection substance for detecting a secretion bound to a substance disposed on the surface of the substrate 410 therethrough.

The detection substance is preferably a labeled substance. For example, in a case where the secretion is an antibody, examples of the detection substance include a labeled antibody which specifically binds to an Fc part or the like of the antibody. Examples of the label include an enzyme label, a fluorescent label, a biotin label, and a label using a radioactive substance.

After sorting the target cell by the method of the present embodiment, the sorted cell can be recovered. A method of recovering the cell captured in the recessed portion of the filter film is not particularly limited. For example, it is possible to perform by using a manipulator, a pipette, or the like.

All technical literature cited in the present specification are incorporated by reference in their entirety.

The terms used in the present specification are used to describe particular embodiments and should not be understood as intending to limit the invention. Unless a different definition is explicitly stated, the terms (including technical terms and scientific terms) used in the present specification are to be regarded as having the same meanings as those widely understood by those skilled in the technical field to which the present invention belongs. It should not be interpreted in an idealized or overly formal sense.

The term "including" used in the present specification is intended to mean that there are described matters (such as a member, a step, an element, and a number), except a case where the context clearly requires a different understanding. It does not exclude the presence of other matters (such as a member, a step, an element, and a number).

In the present specification and claims, unless otherwise specified, as long as there is no conflict in context, the subject expressed by each noun in this specification and claims is intended such that one or a plurality of the subject may exist.

EXAMPLES

Hereinafter, the present invention will be described more specifically using Examples, but the present invention is not limited thereto.

Example 1

Manufacture of Structure Body

A structure body with a shape as shown in FIGS. 4A and 4B was manufactured.

Manufacture of Filter Film

A silicon substrate was coated with a base film forming composition by a spin coater (1500 rpm, 20 seconds) and pre-baked at 90° C. for 1 minute and 120° C. for 3 minutes using a hot plate to form a base film.

Subsequently, the base film was coated with a curable resin composition (see Japanese Unexamined Patent Application, First Publication No. 2008-180877 and Japanese Unexamined Patent Application, First Publication No. 2011-111588) by a spin coater (1500 rpm, 70 seconds) and pre-baked at 60° C. for 2 minutes using a hot plate. Thereafter, pattern exposure was carried out using an i-ray stepper (Model "NSR-2205i14E", manufactured by Nikon Corporation). After exposure at 90° C. for 90 seconds using a hot plate, heating was performed. Thereafter, a development treatment was carried out for 30 seconds by a dipping method using propylene glycol monomethyl ether acetate (PGMEA). Subsequently, each substrate was post-baked using an oven at 120° C. for 1 minute by a resin pattern after the development, to obtain a first film in which the first through-hole and the bottom of the recessed portion are patterned.

Subsequently, the first film was coated with a curable resin composition by a spin coater (1000 rpm, 70 seconds) and pre-baked at 120° C. for 3 minutes using a hot plate. Thereafter, pattern exposure was carried out using an i-ray stepper (Model "NSR-2205i14E", manufactured by Nikon Corporation). After exposure at 120° C. for 2 minutes using a hot plate, heating was performed. Thereafter, a development treatment was carried out for 90 seconds by a dipping method using PGMEA. Subsequently, each substrate was post-baked using an oven at 180° C. for 15 minutes by a resin pattern after the development, to obtain a second film in which a second through-hole continuous with the first through-hole and a side portion of the recessed portion are patterned. As a result, a filter film which is a laminate of the first film and the second film was obtained.

FIG. 1C is a scanning electron micrograph of the manufactured filter film. The manufactured filter film included a recessed portion having a quadrangular prism shape having a square opening in which each side was 15 µm and a through-hole having a quadrangular prism shape in which a short side was 5 µm and a long side is 15 µm. A height of the recessed portion was 15 µm. In addition, a pitch between the recessed portions was 30 µm. The pitch between the through-holes was 30 µm. In addition, the number of the recessed portions present in the whole filter film was $1.5 \times 10^6$.

Separation of Filter Film

The substrate after forming the second film was immersed in a release agent to dissolve the base film. As a result, the filter film was separated from the silicon substrate.

Manufacture of Structure Body

Manufacture of Frame of Structure Body

A frame made of polystyrene was produced by an injection forming.

Bonding of Filter Film and Substrate

The filter film, the substrate made of polystyrene, and the frame were bonded with each other using an adhesive to obtain the structure body of Example 1. The filter film was bonded such that a face (the other face) on a side opposite the face to which the recessed portion opened faced the substrate. The distance between the other face and the substrate of the filter film was 250 μm.

Comparative Example 1

A structure body of Comparative Example 1, with a shape as shown in FIGS. 4A and 4B was manufactured using the same manner as that of Example 1. In the structure body of Comparative Example 1, only a structure of a filter film was different from the structure body of Example 1. The filter film of the structure body of Comparative Example 1 included recessed portions having the same shape, the same size, and the same number as those of the filter film of the structure body of Example 1 but did not include the through-hole.

Experimental Example 1

Evaluation of Capture Efficiency of Cell

Cells were captured using the structure body of Example 1 and Comparative Example 1, and cell capture efficiency was evaluated. As cells to be captured, Namalwa cells stained with Calcein-AM (manufactured by Dojindo Molecular Technologies, Inc.) which is a fluorescent dye for viable cell staining were used. For a medium for cells, RPMI 1640 medium supplemented with fetal bovine serum (FBS) was used.

First, 2 mL of medium was added to the filter film of the structure body of each of Example 1 and Comparative Example 1 such that the filter film and an inside of the structure body were wetted. Subsequently, 5 mL of medium in which the same number of cells ($1.5 \times 10^6$) as the recessed portions present in the filter film were dispersed was added to a face side (one face side) to which the recessed portions of the filter film of each structure body open.

Subsequently, a total of 4 mL of the medium discharged through the flow channel was removed within 1 minute after the addition of the cells, and the medium was allowed to stand as it was. Subsequently, after standing for 10 minutes, fluorescence microscopic observation was performed by focusing on the filter film, and the cells captured in the recessed portions were counted. The number of the recessed portions per field of view of the fluorescence microscope (magnification 10 times) was 989.

Figure 6A:
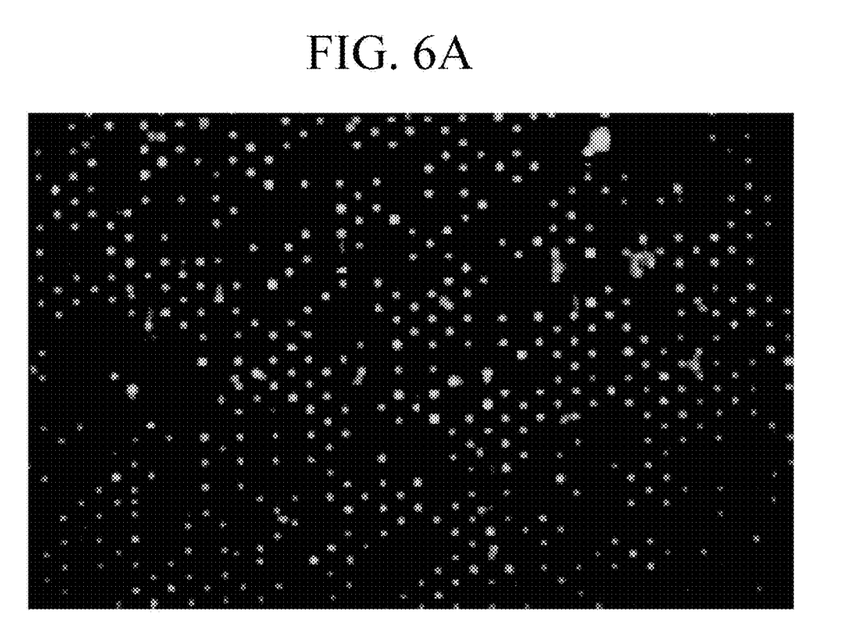
FIG. 6A is a representative fluorescent micrograph of a filter film of a structure body of Example 1, photographed in Experimental Example 1.
Figure 6B:
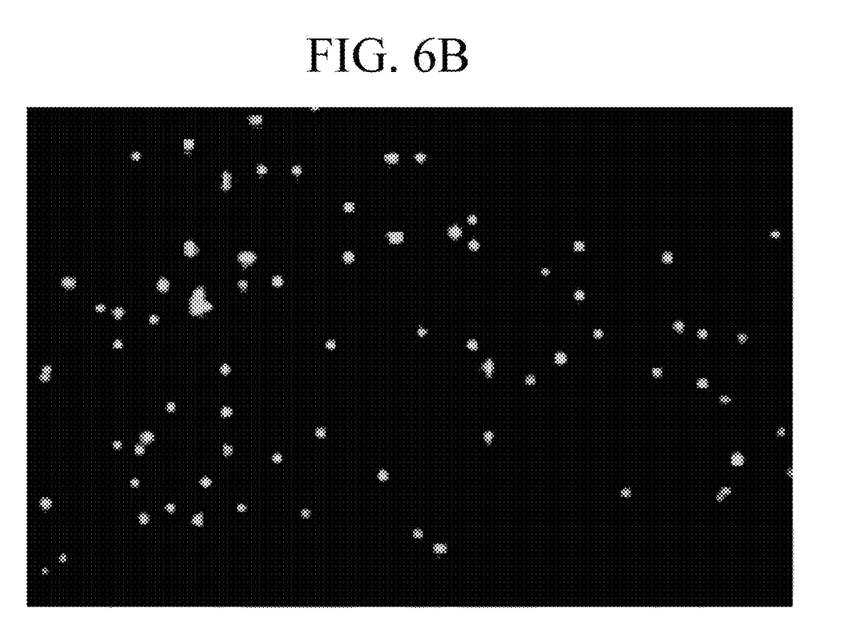
FIG. 6B is a representative fluorescence micrograph of a filter film of a structure body of Comparative Example 1, photographed in Experimental Example 1.

FIG. 6A is a representative fluorescent micrograph of the filter film of the structure body of Example 1. The magnification was 10 times. FIG. 6B is a representative fluorescent micrograph of the filter film of the structure body of Comparative Example 1. The magnification was 10 times. In addition, representative results obtained by counting the cells captured in the recessed portions per field of view are shown in Table 1.

TABLE 1

| | Example 1 | Comparative Example 1 |
|---|---|---|
| Number of cells captured in recessed portions | 519 | 47 |

As a result, it was clear that, according to the filter film of the structure body of Example 1, it is possible to efficiently capture cells.

Experimental Example 2

Sorting of Cells

Using the structure body of Example 1, cells expressing a target protein were sorted. As the target protein, a mouse monoclonal antibody against RANKL, which is a membrane protein, was used.

The gene encoding the monoclonal antibody was introduced to 293FT cells. Subsequently, cells expressing the monoclonal antibody were sorted from a population of 293FT cells into which the gene was introduced.

First, fibronectin (Catalog No. "063-05591", Wako Pure Chemical Corporation) diluted with phosphate buffer (PBS) was introduced from the opening 430 of the structure body of Example 1 so as to be 0.05 mg/mL, and kept at 4° C. overnight. The substrate surface of the structure body was coated with the fibronectin.

Subsequently, PBS was passed through from the opening 430 of the structure body to wash and remove excess fibronectin. Subsequently, CHO-DXB11 cells expressing RANKL which is a membrane protein were introduced from the opening 430 of the structure body, seeded, and cultured for 48 hours.

Subsequently, the 293FT cells into which the antibody gene had been introduced were stained with a fluorescent dye CellBrite™ Orange Cytoplasmic Membrane-Labeling Kit (Model "30022", manufactured by Biotium). Subsequently, 293FT cells stained with the fluorescent dye were seeded on the filter film of the structure body and captured one by one for each recessed portion of the filter film.

Subsequently, Alexa 488-labeled goat anti-mouse IgG antibody (Model "#A11001", manufactured by Life Technology Inc) was diluted 500-fold with an MEMα medium supplemented with fetal bovine serum (FBS), introduced onto the filter film of the structure body, and was allowed to stand in a $CO_2$ incubator for 3 hours. As a result, an antigen-antibody complex including a mouse monoclonal antibody secreted by 293FT cells, a membrane protein expressed by CHO-DXB11 cells on the substrate, and the Alexa 488-labeled goat anti-mouse IgG antibody was formed.

Subsequently, the MEMα medium supplemented with FBS was passed through from the opening 430 of the structure body to perform washing and remove unreacted antibodies. Subsequently, cells were observed with a fluorescence microscope (Model "CKX 41", manufactured by Olympus Corporation).

Figure 7:
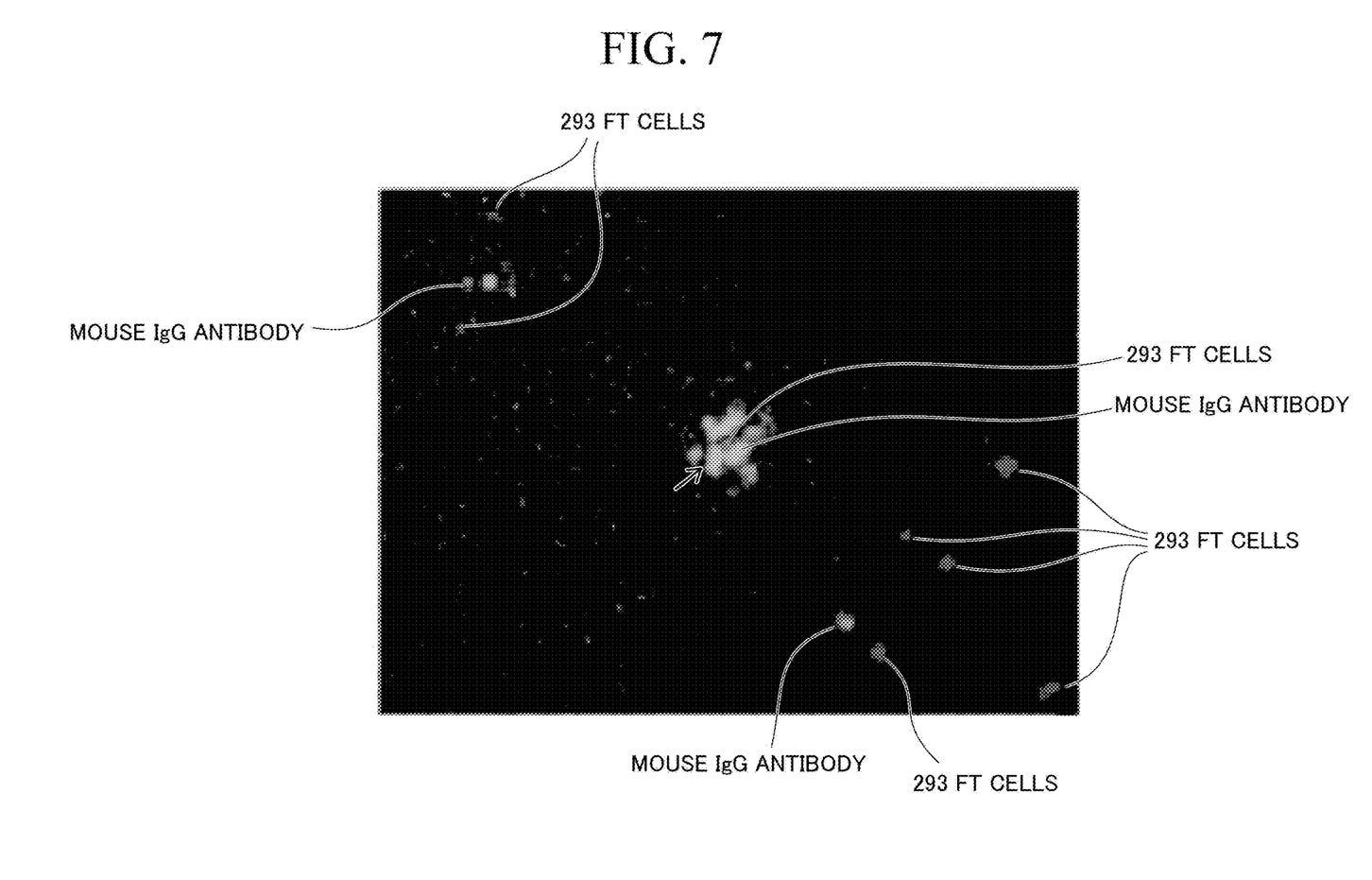
FIG. 7 is a representative fluorescence micrograph of a structure body, photographed from a substrate side, in Experimental Example 2.

FIG. 7 is a representative fluorescence micrograph of the structure body, photographed from a substrate side. As a result, 293FT cells were detected by red fluorescence. In addition, the presence of a mouse monoclonal antibody bound to the membrane protein expressed by CHO-DXB11 cells was detected by green fluorescence, in the vicinity of the targeted 293FT cells which secreted the mouse monoclonal antibody.

As a result of detecting this fluorescence, the 293FT cells expressing the mouse monoclonal antibody could be specified at the single cell level to be sorted. In FIG. 7, the 293FT cells expressing the mouse monoclonal antibody are indicated by an arrow.

While preferred embodiments of the invention have been described and shown above, it should be understood that these are exemplary examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

According to the present invention, it is possible to provide a technology to efficiently capture particles.

EXPLANATION OF REFERENCES 100, 100a, 100b: Filter film
110, 110a, 110b: Through-hole
110z: First through-hole
110y: Second through-hole
120, 120a, 120b: Recessed portion
120z: Bottom of recessed portion
120y: Side portion of recessed portion
130: One face
140: The other face
310: Support
320: Base film
330, 340: Curable resin film
330a: First film
340a: Second film
400: Structure body
410: Substrate
420: Member
430: Opening
P: Particle

What is claimed is:

1. A filter film comprising:
a through-hole; and
a recessed portion having a size capable of capturing one particle,
wherein the recessed portion is open to one face of the filter film,
the through-hole in the one face has a shape or a size such that the one particle is not capable of passing through the through-hole,
the through-hole and the recessed portion are disposed close to each other, and
the recessed portion includes an enclosed bottom.

2. The filter film according to claim 1,
wherein a plurality of the through-holes and a plurality of the recessed portions are provided, and
a ratio (through-holes:recessed portions) between the number of the through-holes and the number of the recessed portions is 1:5 to b 100:1.

3. The filter film according to claim 1, wherein a projected area-equivalent diameter of the one particle is 0.01 μm or more and 1 mm or less.

4. The filter film according to claim 1,
wherein the particle includes a cell, and
the filter film is used for capturing the cell.

5. The filter film according to claim 1, wherein the through-hole and the recessed portion are disposed such that a distance between a centroid of the shape of the through-hole on the face and a centroid of the shape of the recessed portion on the face is 0.5 to 10 times the diameter of a circle having the same area as the projected area of the particle.

6. The filter film according to claim 1, wherein the recessed portion is disposed on the face of the filter film at a portion where the through-hole is not formed in a plane view of the face.

7. The filter film according to claim 1, wherein the through-holes and recessed portions are interspersed throughout the film.

8. A method of manufacturing the filter film according to claim 1, the method comprising:
laminating a dissolvable base film on a support;
laminating a first curable resin film on the base film;
patterning the first curable resin film to obtain a first film in which a first through-hole and a bottom of the recessed portion are patterned;
laminating a second curable resin film on the first film;
patterning the second curable resin film to obtain a second film in which a second through-hole continuous with the first through-hole and a side portion of the recessed portion are patterned; and
dissolving the base film to separate a laminate of the first film and the second film, which is to be the filter film, from the support.

9. A structure body comprising:
the filter film according to claim 1; and
a substrate disposed apart from the filter film so as to face the other face of the filter film.

10. A method of capturing a particle, comprising bringing a dispersion liquid of the particle into contact with a face, of the filter film according to claim 1 on a side to which the recessed portion is open.

11. The method of capturing a particle according to claim 10, wherein the particle includes a cell.

12. A method of sorting cells, by which a target cell secreting a secretion is sorted from a plurality of the cells, the method comprising:
bringing a dispersion liquid of the cells into contact with a face, of the filter film of the structure body according to claim 9, on a side to which the recessed portion is open, to capture one unit of the cells per the recessed portion;
causing the cells captured in the recessed portion to secrete the secretion and causing the secretion to be accumulated on an area of a surface of the substrate close to the recessed portion;
detecting a change caused by accumulation of the secretion; and
sorting the target cell using the change as an index.

13. The method of sorting cells according to claim 12, wherein on the surface of the substrate, an expressing cell of a biomolecule having an affinity for the secretion is laminated, the biomolecule having an affinity for the secretion is laminated, or a compound having an affinity for the secretion is laminated.

* * * * *